(12) United States Patent
Shinge et al.

(10) Patent No.: US 11,066,354 B2
(45) Date of Patent: Jul. 20, 2021

(54) PROCESS FOR MONO N-ALKYLATION OF AMINOPHENOL

(71) Applicant: SABIC GLOBAL TECHNOLOGIES B.V., Bergen op Zoom (NL)

(72) Inventors: Prashant Sukumar Shinge, Geleen (NL); Jaiprakash Brijlal Sainani, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/621,767

(22) PCT Filed: Jun. 11, 2018

(86) PCT No.: PCT/EP2018/065328
§ 371 (c)(1),
(2) Date: Dec. 12, 2019

(87) PCT Pub. No.: WO2018/228981
PCT Pub. Date: Dec. 20, 2018

(65) Prior Publication Data
US 2020/0140373 A1 May 7, 2020

(30) Foreign Application Priority Data
Jun. 14, 2017 (EP) ..................................... 17176070

(51) Int. Cl.
*C07C 213/08* (2006.01)
*C07C 215/76* (2006.01)

(52) U.S. Cl.
CPC .......... *C07C 213/08* (2013.01); *C07C 215/76* (2013.01)

(58) Field of Classification Search
None
See application file for complete search history.

(56) References Cited

U.S. PATENT DOCUMENTS 9,278,905 B2   3/2016   Ohshima et al.
2004/0127747 A1   7/2004   Selva et al.

FOREIGN PATENT DOCUMENTS

DE                953169 C       11/1956

OTHER PUBLICATIONS

Zukowska et al. (Organometallics, 2012, 31(1), 462) (Year: 2012).*
Cho Yeon-Ho et al: "Cyanide as a powerful catalyst for facile synthesis of benzofused heteroaromatic compounds via aerobic oxidation", Tetrahedron, Elsevier Science Publishers, Amsterdam, NL, vol. 69, No. 32, Jun. 7, 2013 (Jun. 7, 2013), pp. 6565-6573, XP028573202.
European Seach Report for European Application No. 17176070.5 dated Nov. 20, 2017, 9 pages.
International Search Report for International Application No. PCT/EP2018/065328, International Filing Date Jun. 11, 2018, dated Aug. 10, 2018, 7 pages.
Kalgutkar A S et al. "Covalent modification of cyclooxygenase-2 (COX-2) by 2-acetoxyphenyl alkyl sulphides, a new class of selective COX-2 inactivators", Journal of Medicinal Chemistry, American Chemica Society, vol. 41, No. 24, Nov. 19, 1998, pp. 4800-4818.
L Galatis, "Uber das Acetat des N-Methyl-p-amino-phenols", Chemische Berichte, Jan. 1, 1927, p. 1399-1402.
Layer R W: "The Chemistry of Imines", Chemical Reviews, American Chemical Society, US, vol. 63, Jan. 1, 1963 (Jan. 1, 1963), pp. 489-510, XP001056730.
Matralis et al. "Novel Benzoxazine and Benzothiazine Derivatives as Multifunctional Antihyperlipidemic Agents" Journal of Medicinal Chemistry, Published Jun. 27, 2011, 5583-5591.
Ozturk Bengi Ozgun et al: "In situ medication of the Grubbs first generation catalyst: A highly controllable metathesis catalyst bearing tridentate Schiff base ligands", Journal of Molecular Catalysis A: Chemical, Elsevier, Amsterdam, NL, vol. 376, Apr. 17, 2013 (Apr. 17, 2013), pp. 53-62, XP028565217.
Sakurai et al. "Tertiary Amine-Catalyzed Acyl Group-Exchange Reactions of N,O-Diacyl-o-aminophenols", The Chemical Society of Japan, Bull. Chem. Soc. Jpn., vol. 59, No. 8, (1986), 2666-2668.
Written Opinion for International Application No. PCT/EP2018/065328, International Filing Date Jun. 11, 2018, dated Aug. 10, 2018, 8 pages.

* cited by examiner

*Primary Examiner* — Sudhakar Katakam
*Assistant Examiner* — Jennifer C Sawyer
(74) *Attorney, Agent, or Firm* — Cantor Colburn LLP

(57) ABSTRACT

The invention relates to a process for the preparation of a compound represented by formula (I) wherein X is selected from the group consisting of —H, -halogen, linear or branched C1-C7 alkyl group, linear or branched C1-C5 alkoxy group, —NO$_2$ and —CN and Y is a linear or branched C1-C7 alkyl group, comprising the steps of: 10 a) reacting a compound represented by formula (II) with a compound represented by (III) to obtain an intermediate product, wherein X is as defined with respect to formula (I), wherein Z is H, CH$_3$ or C$_2$H$_5$, b) reacting the intermediate product of step a) with a compound represented by Y$_2$SO$_4$ (IV) wherein Y is as defined with respect to formula (I) to obtain a salt and c) hydrolyzing the salt of step b) to obtain the compound of formula (I).

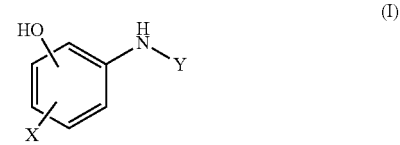

(I)

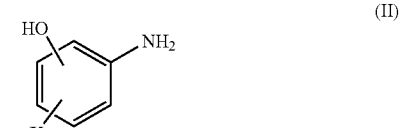

(II)

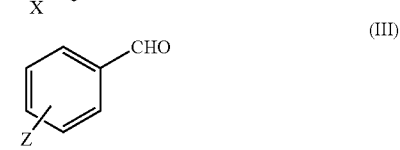

(III)

11 Claims, No Drawings

PROCESS FOR MONO N-ALKYLATION OF AMINOPHENOL

CROSS REFERENCE TO RELATED APPLICATIONS

This application is a National Stage application of PCT/EP2018/065328, filed Jun. 11, 2018, which claims the benefit of European Application No. 17176070.5, filed Jun. 14, 2017, both of which are incorporated by reference in their entirety herein.

The present invention relates to a process for mono n-alkylation of an aminophenol.

N-monoalkyl derivatives of aminophenols are important synthetic intermediates in organic synthesis which are used in the synthesis of pharmaceutical drug intermediates, ligands for asymmetric catalyst and donors for propylene, ethylene catalyst. However, a mixture of N-mono and di-N or mixture of O- and N-alkyl is obtained when it is alkylated directly without good selectivity and it involves tedious purification methods with low yields. Such methods are not environmental friendly on an industrial scale. For example, Kalgutkar et. al., J. Med. Chem. 1998, 41, 4800-4818 describes such process.

US2004127747 describes a process for the direct synthesis of mono-N-substituted anilines by the reaction of an aniline compound with an organic carbonate in the presence of a faujasite.

L Galatis, "Uber das Acetat des N-Methyl-p-amino-phenols", Chemische Berichte, 1 Jan. 1927, p. 1399-1402 discloses reacting benzal-p-amino-phenol with Et2SO4 at 100-105° C. to obtain N-ethyl-p-aminophenol. This document does not mention monoalkylation of aminophenol.

There is still a need in the art for a process for the preparation of mono-N-alkyl-aminophenol in one step with high yields.

It is an objective of the present invention to provide a process for the preparation of mono-N-alkyl-aminophenol in one step with high yields.

Accordingly, the present invention provides a process for the preparation of a compound represented by formula (I)

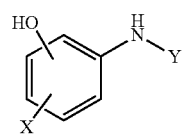
(I)

wherein

X is selected from the group consisting of —H, halogen, linear or branched C1-C7 alkyl group, linear or branched C1-C5 alkoxy group, —NO$_2$ and —CN and Y is a linear or branched C1-C7 alkyl group, comprising the steps of:

a) reacting a compound represented by formula (II) with a compound represented by (III) to obtain an intermediate product,

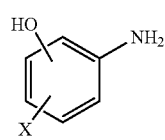
(II)

wherein X is as defined with respect to formula (I),

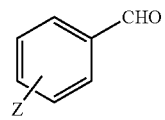
(III)

wherein Z is H, H$_3$ or c$_2$H$_5$, b) reacting the intermediate product of step a) with a compound represented by Y$_2$SO$_4$ (IV) wherein Y is as defined with respect to formula (I) to obtain a salt and c) hydrolyzing the salt of step b) to obtain the compound of formula (I).

According to the process of the invention, N-monoalkyl derivative of an aminophenol is obtained with good selectivity without purification steps. The process is environmental and industrial friendly.

Step a)

In step a), the compound (II) is reacted with the compound (III). The amino group of the compound (II) reacts with the aldehyde group of the compound (III) to give an intermediate product.

In compound (II), —OH group can be ortho, meta or para with respect to the carbon atom to which the nitrogen atom is attached. Preferably, the —OH group is ortho with respect to the carbon atom to which the nitrogen atom is attached.

In compound (II), X can be ortho, meta or para with respect to the carbon atom to which the nitrogen atom is attached. Preferably, X is meta with respect to the carbon atom to which the nitrogen atom is attached. Preferably, X is —H or a linear or branched C1-C7 alkyl, more preferably —H or —CH$_3$ or —C$_2$H5.

In compound (II), preferably, the —OH group is ortho with respect to the carbon atom to which the nitrogen atom is attached and X is meta with respect to the carbon atom to which the nitrogen atom is attached.

In compound (III), Z can be ortho, meta or para with respect to the carbon atom to which the aldehyde group is attached.

In compound (III), Z is preferably H.

Step a) is performed such that the amino group of the compound (II) reacts with the aldehyde group of the compound (III) to form —N═C—. This can be performed by any known method. For example, step a) may be performed in the presence of a reagent for nitration of aromatic compounds, such as copper (II) nitrate. Step a) may be performed in the presence of appropriate solvents such as water and ethanol.

The reaction may be performed at room temperature. The duration of the reaction may e.g. be 0.5-5 hours.

After completion of the reaction no purification step is necessary before step b).

Step b)

In step b), the intermediate product of step a) is reacted with a compound represented by Y$_2$SO$_4$ (IV), a dialkyl sulfate. Y is preferably —CH$_3$ or —C$_2$H$_5$, most preferably —CH$_3$.

This can be performed by any known method. For example, step b) may be performed in the presence of an organic solvent such as toluene.

The reaction may be performed e.g. at temperatures of 60-100° C., preferably 70-75° C. The duration of the reaction may e.g. be 0.5-5 hours. An N-alkyl quaternary salt is formed.

After completion of the reaction no purification step is necessary before step c).

Step c)

In step c), the N-alkyl quaternary salt is hydrolyzed to obtain the compound of formula (I). The compound (III) is almost completely recovered and can be recycled after distillation.

The hydrolysis may be performed by the addition of HCl solution.

The reaction may be performed e.g. at 40-70° C.

After completion of the hydrolysis, the compound (I) and the compound (III) may be isolated from the reaction mixture by known methods.

In an embodiment, the compound (II) is 2-aminophenol, the compound (III) is benzaldehyde, the compound (IV) is dimethyl sulfate. 2-methylaminophenol as the compound (I) is obtained. The reaction of step a) is as follows:

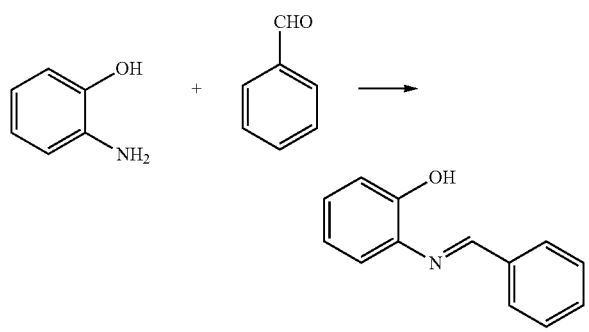

The reaction of steps b) and c) is as follows:

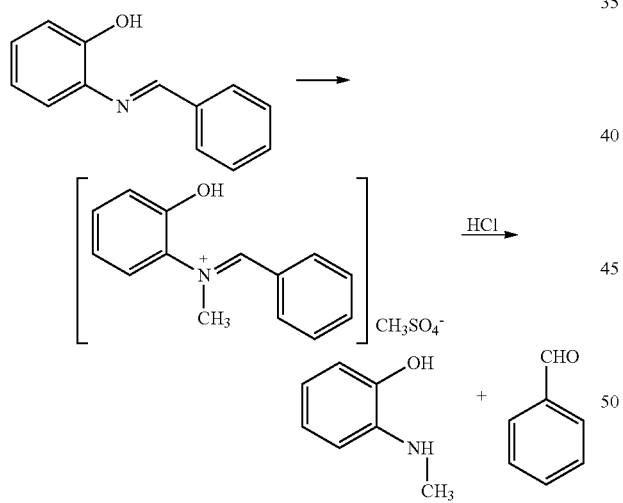

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

The invention is now elucidated by way of the following examples, without however being limited thereto.

EXAMPLES

Example 1

2-(Benzylideneamino)phenol

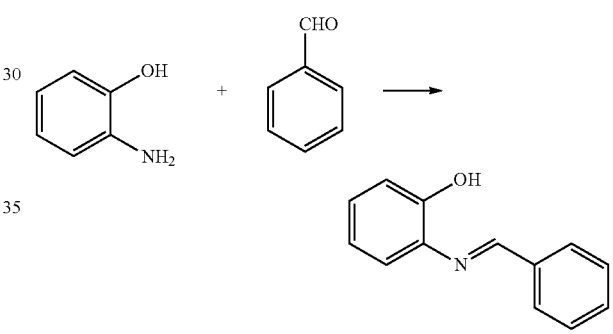

To a stirred solution of 2-aminophenol (10.91 gm; 0.1 mol) in 60 ml ethanol was added benzaldehyde (10.6 gm; 0.1 mol) and Cu(NO$_3$)$_2$.6H$_2$O (1 mol %) and the resulting solution was stirred at room temperature for 1-2 hours. After completion of reaction water 100 ml was added to give brown solid, m.p.: 112-116° C. as 2-(benzylideneamino) phenol 18.1 gm (91%), (TLC single spot).

2-(methylamino)phenol

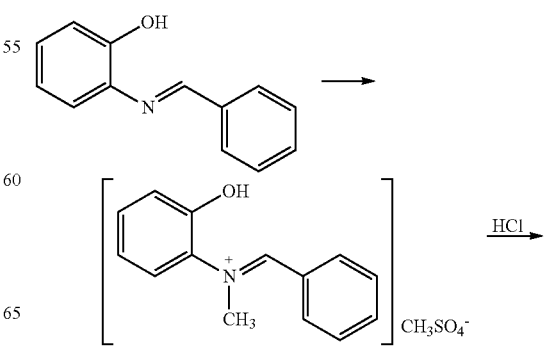

-continued

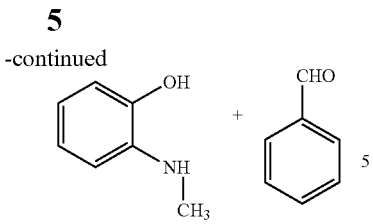

A solution of 2-(benzylideneamino)phenol (10 gm, 0.05 mol), dimethyl sulfate (6.3 gm, 0.05 mol) and 70 ml toluene were mixed and heated to 70-75° C. for 1-2 hours to form complex. The reaction mixture was cooled to 40-50° C. and 50 ml dilute HCl solution was gradually added. The mixture was warmed to 60-65° C. for 30 min to complete hydrolysis and then cooled to room temperature. The bottom aqueous layer was separated from upper toluene layer, which contains benzaldehyde. The aqueous acidic solution was basified with dilute sodium carbonate solution to give 2-methylaminophenol 5.2 gm (85%), m.p. 89-93° C. (TLC single spot)

Example 2

2-(Benzylideneamino)-4-(tertbutyl)phenol

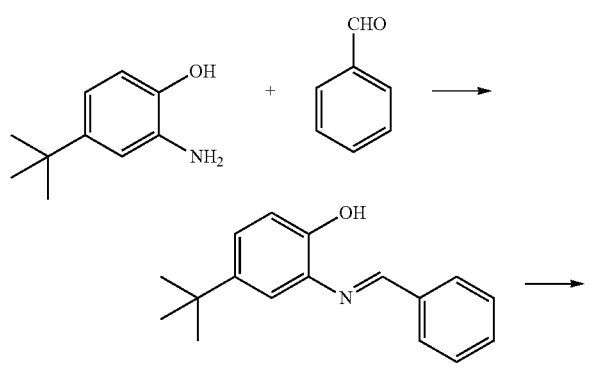

To a stirred solution of 2-amino-4-tert-butylphenol (16.5 gm; 0.1 mol) in 90 ml ethanol was added benzaldehyde (10.6 gm; 0.1 mol) and Cu(NO$_3$)$_2$.6H$_2$O (1 mol %) at room temperature. The resulting solution was stirred under nitrogen at room temperature for 2-4 hours. After completion of reaction (checked by TLC), water 125 ml was added to give solid, as 2-(benzylideneamino)-4-(tertbutyl)phenol 22.7 gm (89%), (TLC single spot).

2-(methylamino)-4-(tertbutyl)phenol

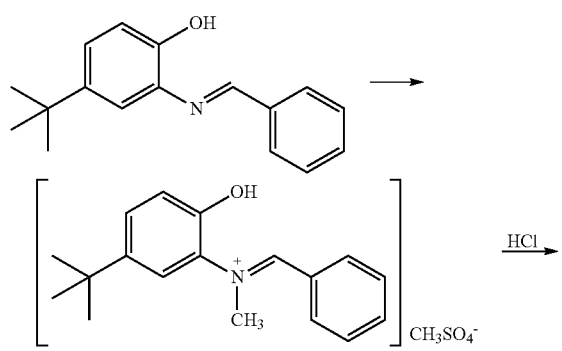

A solution of 2-(benzylideneamino)-4-(tertbutyl)phenol (10 gm, 0.04 mol), dimethyl sulfate (6.3 gm, 0.05 mol) and 70 ml toluene were mixed and heated to 70-75° C. for 1-2 hours to form complex. The reaction mixture was cooled to 30° C. and 50 ml dilute HCl solution was gradually added. The mixture was warmed to 70-75° C. for 30 min to complete hydrolysis and then cool to room temperature. The bottom aqueous layer was separated from upper toluene layer, which contains benzaldehyde which was recovered by distillation (85%). The aqueous acidic solution was basified with dilute sodium carbonate solution to give 2-methylamino-4-tertbutyl-phenol 6.44 gm (92%), m.p. 140-45° C. (TLC single spot)

The invention claimed is:

1. A process for the preparation of a compound represented by formula (I)

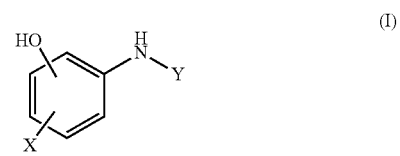

wherein
X is selected from the group consisting of —H, a halogen, linear or branched C1-C7 alkyl group, linear or branched C1-C5 alkoxy group, —NO$_2$ and —CN and
Y is a linear or branched C1-C7 alkyl group,
comprising the steps of:
a) reacting a compound represented by formula (II) with a compound represented by (III) to obtain an intermediate product,

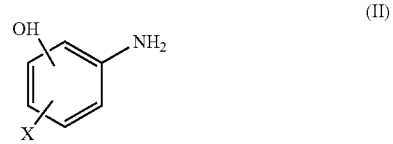

wherein X is as defined with respect to formula (I), wherein Z is H, —CH$_3$ or —C$_2$H$_5$,
b) reacting the intermediate product of step a) with a compound represented by Y$_2$SO$_4$ (IV) wherein Y is as defined with respect to formula (I) to obtain a salt and
c) hydrolyzing the salt of step b) to obtain the compound of formula (I).

2. The process according to claim 1, wherein the —OH group is ortho with respect to the carbon atom to which the —NH$_2$ group is attached in compound (II).

3. The process according to claim 1, wherein X is —H or a linear or branched C1-C7 alkyl group in compound (II).

4. The process according to claim 1, wherein Z is —H in compound (III).

5. The process according to claim 1, wherein step a) is performed in the presence of a reagent for nitration of an aromatic compound.

6. The process according to claim 1, wherein Y is —CH$_3$ or —C$_2$H$_5$ in compound (IV).

7. The process according to claim 1, wherein step b) is performed in the presence of an organic solvent.

8. The process according to claim 1, wherein step c) is performed by the addition of HCl solution to the salt of step b).

9. The process according to claim 5, wherein the aromatic compound is copper (II) nitrate.

10. The process according to claim 6, wherein Y is —CH$_3$ in compound (IV).

11. The process of claim 7, wherein the organic solvent is toluene.

\* \* \* \* \*